(12) United States Patent
Maughan et al.

(10) Patent No.: US 7,756,728 B2
(45) Date of Patent: Jul. 13, 2010

(54) HEALTHCARE SYSTEM AND USER INTERFACE FOR CONSOLIDATING PATIENT RELATED INFORMATION FROM DIFFERENT SOURCES

(75) Inventors: Rex Wendell Maughan, Murray, UT (US); Jeffry Brent Jacobsen, Logan, UT (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 2823 days.

(21) Appl. No.: 10/282,644

(22) Filed: Oct. 29, 2002

(65) Prior Publication Data

US 2003/0088438 A1    May 8, 2003

Related U.S. Application Data

(60) Provisional application No. 60/335,976, filed on Oct. 31, 2001.

(51) Int. Cl.
*G06F 19/00* (2006.01)
*G06Q 50/00* (2006.01)

(52) U.S. Cl. .............................. 705/3; 705/2

(58) Field of Classification Search ............ 705/2, 705/3
See application file for complete search history.

(56) References Cited

U.S. PATENT DOCUMENTS

| | | | |
|---|---|---|---|
| 5,506,984 A * | 4/1996 | Miller | 1/1 |
| 5,544,044 A * | 8/1996 | Leatherman | 705/3 |
| 5,560,005 A | 9/1996 | Hoover et al. | 396/600 |
| 5,664,109 A | 9/1997 | Johnson et al. | 705/2 |
| 5,724,575 A | 3/1998 | Hoover et al. | 395/610 |
| 5,737,539 A * | 4/1998 | Edelson et al. | 705/3 |
| 5,899,998 A | 5/1999 | McGauley et al. | 707/104 |
| 5,903,889 A * | 5/1999 | de la Huerga et al. | 707/3 |
| 6,988,075 B1 * | 1/2006 | Hacker | 705/3 |
| 2001/0051879 A1 | 12/2001 | Johnson et al. | 705/2 |
| 2001/0051880 A1 | 12/2001 | Schurenberg et al. | 705/3 |
| 2001/0051881 A1 * | 12/2001 | Filler | 705/3 |
| 2002/0007284 A1 | 1/2002 | Schurenberg et al. | 705/2 |

FOREIGN PATENT DOCUMENTS

| | | |
|---|---|---|
| EP | 1 077 415 | 2/2001 |
| WO | WO 98 13783 | 4/1998 |

(Continued)

OTHER PUBLICATIONS

Kilman, An international collaboratory based on virtual patient records, Aug. 1997, ACM Press, Communications of the ACM, vol. 40, Issue 8, pp. 110-117.*

(Continued)

*Primary Examiner*—Robert W Morgan
*Assistant Examiner*—Tran Nguyen

(57) ABSTRACT

In a healthcare system, a method consolidates patient related information from multiple, different sources by performing the following steps. Patient identification data identifying a particular patient is received. Messages are generated for communication to a corresponding information sources. The generated messages incorporate the particular patient identification data and a request for information concerning the particular patient. The messages are communicated to the corresponding information sources. Response messages are received containing requested information concerning the particular patient from the information sources. The requested information is sorted and merged from the response messages to provide data representative of consolidated patient related information.

23 Claims, 8 Drawing Sheets

FOREIGN PATENT DOCUMENTS

| | | |
|---|---|---|
| WO | WO 99 44162 | 9/1999 |
| WO | WO 00 65522 | 11/2000 |

OTHER PUBLICATIONS

Forslund, The Virtual Patient Record: A Key to Distributed Healthcare and Telemedicine, Feb. 29, 1996, http://www.acl.lang.gov/TeleMed/Papers/virtual.html.*

Brelstaff, Internet Patient Records: new techniques, Mar. 17, 2001, J Med Internet Res. Jan.-Mar. 2001; 3(1): e8.*

Sheth, Federated Database Systems for Managing Distributed, Heterogeneous, and Autonomous Databases, Sep. 1990, ACM Computing Survey, vol. 22, No. 3, p. 183-236.*

Demers, Epidemic algorithms for replicated database maintenance, Aug. 10, 1987, Proceedings of the sixth annual ACM Symposium on Principles of distributed computing, Vancouver, British Columbia, Canada, p. 1-12.*

Kilman, An international collaboratory based on virtual patient records, Aug. 1997, ACM Press, Communications of the ACM, vol. 40, Issue 8, pp. 110-117.*

* cited by examiner

Display Window – Patient List
600

Display Window – List Of Healthcare
Sources Related To A Patient
700

Display Window – Healthcare Source Information Related To A Patient
800

HEALTHCARE SYSTEM AND USER INTERFACE FOR CONSOLIDATING PATIENT RELATED INFORMATION FROM DIFFERENT SOURCES

CROSS-REFERENCE TO RELATED APPLICATIONS

The present application is a non-provisional application of provisional application having Ser. No. 60/335,976 filed by Rex Maughan et al. on Oct. 31, 2001.

FIELD OF THE INVENTION

The present invention generally relates to healthcare information systems. More particularly, the present invention relates to a healthcare system and user interface for consolidating patient related information from different sources and a method therefor.

BACKGROUND OF THE INVENTION

Modern healthcare requires the provision of services by many healthcare workers to many patients. In order to accomplish this, healthcare delivery has been organized into specialized departments or healthcare sources such as, for example, nursing, laboratory, pharmacy, and radiology departments. Each department has responsibility for accomplishing its particular, often specialized, subset of tasks. Sometimes the departments are associated with different healthcare enterprises or offices having different geographic locations. Unfortunately, this has resulted in sub-optimal healthcare operations because patient information related to a single patient that is stored at various departments is not easily accessible from a single place.

Present healthcare information systems (HIS) combine the patient related information for a particular patient from multiple, different healthcare sources into a single consolidated database, having a master patient index (MPI), using various record matching techniques. However, many problems are encountered in trying to match patient information, received from the multiple, different healthcare sources, to a particular patient. Sometimes the record matching techniques incorrectly combines patient information that is not related to the same patient (i.e., a "false match"), combines the same patient information more than one time for the same patient (i.e., a "duplicate match"), and does not combine patient information that was related to the same patient (i.e., a "miss match"). Present record matching techniques generate a correct match for over 90% of the stored patient information, generate a duplicate match for 5% to 10% of the stored patient information, and generate less than 5% of miss matches of the stored patient information. The reliability of the present record matching techniques reduces the confidence level of users of the MPI, especially when relied upon for the delivery of healthcare. Hence, the present record matching techniques generate an unacceptable number of false matches, duplicate matches, and miss matches.

Present systems require computer servers, having large memory capacity and powerful processors, which are expensive. The large memory capacity stores the patient information for each patient that is received from the multiple, different healthcare sources. The memory in the computer servers stores a copy of the patient information received from the multiple, different healthcare sources. Hence, the memory in the computer server must be as large as the combined memory storage capacity of each of the multiple, different healthcare sources. Such a large memory capacity is expensive. The processor must be powerful enough to combine, by adding, updating, purging, and matching, etc., a large amount of patent information received from multiple, different healthcare sources. Such a processor that can handle such complex and computer intensive tasks is also expensive.

Because of the memory and processor demands on the computer servers, various approaches have been taken to efficiently operate the HIS. For example, one approach is to permit the computer server to receive only a small subset of the available patient information for processing and storage responsive to such limitations such as date, healthcare source, type of illness, etc. Another approach is to standardize the collection of the patent information, using recommended minimum memory capacity, to reduce the number of duplicate matches.

Another problem with present systems is the format of the patient information and clinical result data. For example, a White Blood Count may be called a 'WBC,' a 'White Count,' or a 'WC' at the multiple, different hospital sources. Present systems use stored conversion tables or other techniques to create a common format for the MPI. Although the conversion tables and other techniques are generally successful, they do not provide a 100% correct translation. Clinical result data also needs to be combined and has similar combination problems such as data format, units of measure, normal ranges, and other related significant medical information.

Present systems typically update the MPI on a non-real time basis using various download techniques, such as batch, magnetic tape, diskette, batch direct communications, resulting in a MPI that is not current. Usually, real time updates are prevented by the amount of work for the computer server to combine, translate, index, and match the patient information, as well as particular interface implementations, communication methods, database capabilities, and design implementations.

Some present systems require efficient cooperation between the computer server and the computers located at the multiple, different healthcare sources to provide detailed mapping required for implementing the MPI. Such efficient cooperation typically requires hardware and/or software to be added to one or more of the computers, which adds cost and complexity.

Other present systems depend on many procedural methods to improve the quality of the patient information combined into the MPI. The quality of the patient information varies widely due to such variables as the differences in data collected, admission processes, training, data available, individual usage and interface systems. Although the procedural methods improve the quality of the patient information in the MPI, the level of data quality cannot reach 100% because of the large number of variables, some related to human interaction.

Still other present systems combine the patient information from the multiple, different healthcare sources into a single view. The single view makes is very difficult to see the specific result in context of the original patient information. For example, if all of the blood pressure observations for a patient are combined, it is difficult to determine the medical context for a specific office visit, health problem, hospital stay, etc.

In light of these and other deficiencies, it would be desirable to have a HIS that accurately represents the patient information received from the multiple, different healthcare systems. Such a desirable HIS would have reasonable cost and complexity to permit small and medium sized healthcare providers to implement a system having the MPI. It would be desirable for the HIS to represent in real time all of the patient information available in the original format and context used by the multiple, different healthcare systems, without being confusing or complex. Accordingly, there is a need for a healthcare system and user interface for consolidating patient related information from different sources and corresponding method that would meet these and other desirable features of a healthcare information system.

SUMMARY OF THE INVENTION

In a healthcare system, a method consolidates patient related information from multiple, different sources by performing the following steps. Patient identification data identifying a particular patient is received. Messages are generated for communication to a corresponding information sources. The generated messages incorporate the particular patient identification data and a request for information concerning the particular patient. The messages are communicated to the corresponding information sources. Response messages are received containing requested information concerning the particular patient from the information sources. The requested information is sorted and merged from the response messages to provide data representative of consolidated patient related information.

These and other aspects of the present invention are further described with reference to the following detailed description and the accompanying figures, wherein the same reference numbers are assigned to the same features or elements illustrated in different figures. Note that the figures may not be drawn to scale. Further, there may be other embodiments of the present invention explicitly or implicitly described in the specification that are not specifically illustrated in the figures and visa versa.

DETAILED DESCRIPTION OF THE PREFERRED EMBODIMENTS

Figure 1:
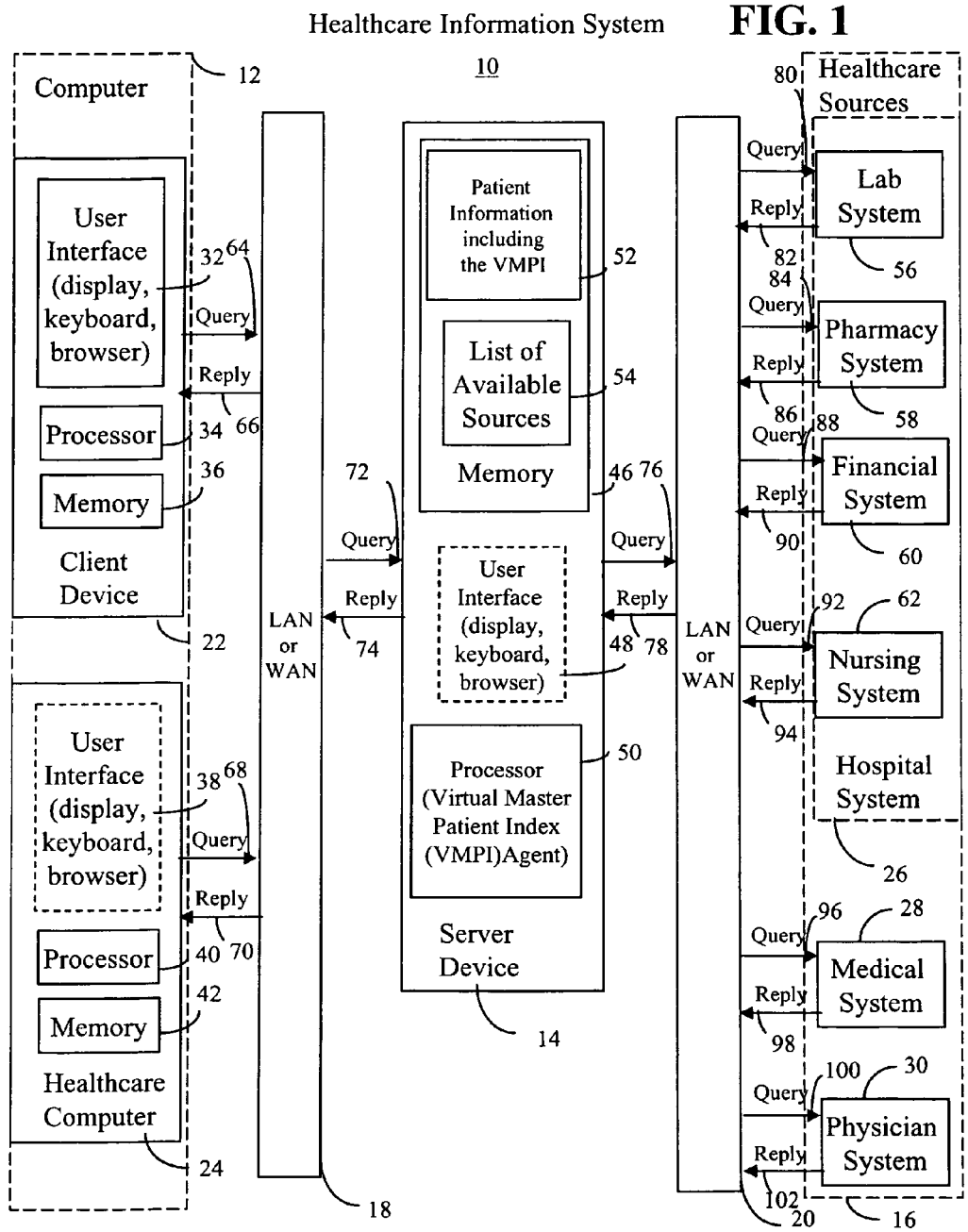
FIG. 1 illustrates a healthcare information system including a computer, a server device, and healthcare sources, in accordance with a preferred embodiment of the present invention.

FIG. 1 illustrates a healthcare information system 10, including a computer 12, a server device 14, and healthcare sources 16, otherwise called information sources, in accordance with a preferred embodiment of the present invention. A first network 18 electrically couples the computer 12 to the server device 14. A second network 20 electrically couples the server device 14 to the healthcare sources 16.

The healthcare information system 10 is intended for use by a healthcare provider that is responsible for monitoring the health and/or welfare of people in its care. Examples of healthcare providers include, without limitation, a hospital, a nursing home, an assisted living care arrangement, a home health care arrangement, a hospice arrangement, a critical care arrangement, a health care clinic, a skilled nursing facility, a physical therapy clinic, a chiropractic clinic, and a dental office. In the preferred embodiment of the present invention, the healthcare provider is a hospital. Examples of the people being serviced by the healthcare provider include, without limitation, a patient, a resident, and a client.

The computer 12 generally includes a client device 22 and/or a healthcare computer 24. Generally, the computer 12 may be considered a requesting device that receives information responsive to making requests. The computer 12 may include one or more client devices 22 and/or one or more healthcare computers 24 that are located at the same or different physical or geographic locations. Preferably, the computer 12 may reside at one of the healthcare sources 16, permitting the computer 12 to be a requesting device as well as an information source. Although each of the client device 22, the healthcare computer 24, the server device 14, and each of the healthcare sources 16 may be generally described as computers, the term computer 12 is used to generally encompass the nature of each of the client device 22 and the healthcare computer 24. The primary difference between the client device 22 and the healthcare computer 24 is that the client device 22 has a user interface 32 and that the healthcare computer 24 does not have a user interface intended for the end user. This distinction relates to the particular function of the computer 12 and to the format of the data sent to the computer 12 by the server device 14. Generally, the client device 22 functions to serve an end user; therefore, the data is formatted for the user interface, such as in hypertext markup language (HTML) for a browser. Whereas, the healthcare computer 24 functions to serve it self or other computers; therefore, the data is formatted for the computer, such as in extensible markup language (XML). Of course, the healthcare computer 24 may ultimately be connected to a user interface adapted for the end user to access the data. In this case, the XML format must be converted to HTML for a browser. Hence, the difference between the client device 12 and the healthcare computer 24 may blur or overlap depending on the particular implementation of the computer 12.

Figure 6:
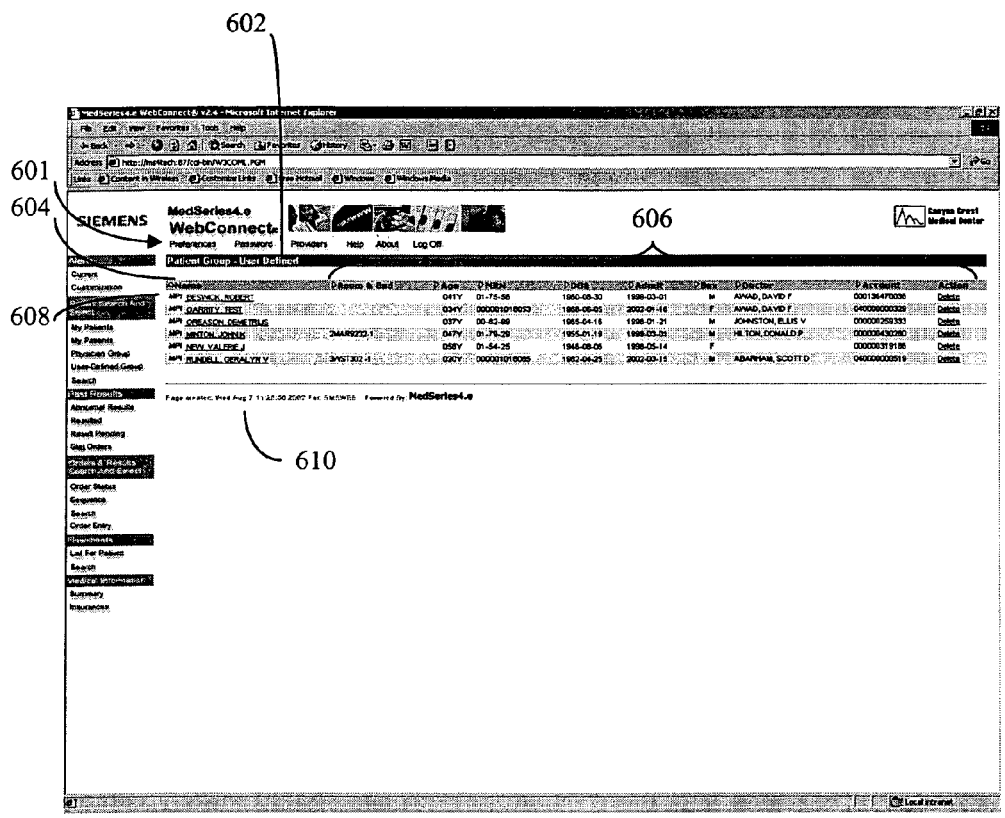
FIG. 6 illustrates a display window showing a patient list, in accordance with a preferred embodiment of the present invention.

The client device 22 generally includes a user interface 32, a processor 34, and a memory unit 36. The user interface 32 generally includes an input device and an output device. Preferably, the memory unit 36 stores patient information, as shown in FIG. 6, that is local to the client device 12. For example, the client device 22 may reside at a medical center and the patient information represents only the patients that come to the medical center for care. The patient information in the memory unit 36 may include the same information as described for the patient information 52 for the server device 14 below, with the exception that the memory unit 36 stores a local patient index (LPI), as shown in FIG. 6, rather than a master patient index (MPI). The client device 12 is preferably implemented as a personal computer. The personal computer may be fixed or mobile and may be implemented in a variety of forms including, without limitation, a desktop, a laptop, a personal digital assistant (PDA), and a cellular telephone. The user interface 32, the processor 34, and the memory unit 36 are constructed and generally operate in a manner well known to those skilled in the art of the design of client devices.

The healthcare computer 24 generally includes an optional user interface 38, a processor 40, and a memory unit 42. Preferably, the memory unit 42 stores patient information, as shown in FIG. 6, that is local to the healthcare computer 24 in a similar manner to that described above for the memory unit 36 in the client device 22. The healthcare computer is preferably implemented as a server device or a workstation. The user interface 38, the processor 40, and the memory unit 42 are constructed and generally operate in a manner well known to those skilled in the art of the design of server devices.

Figure 7:
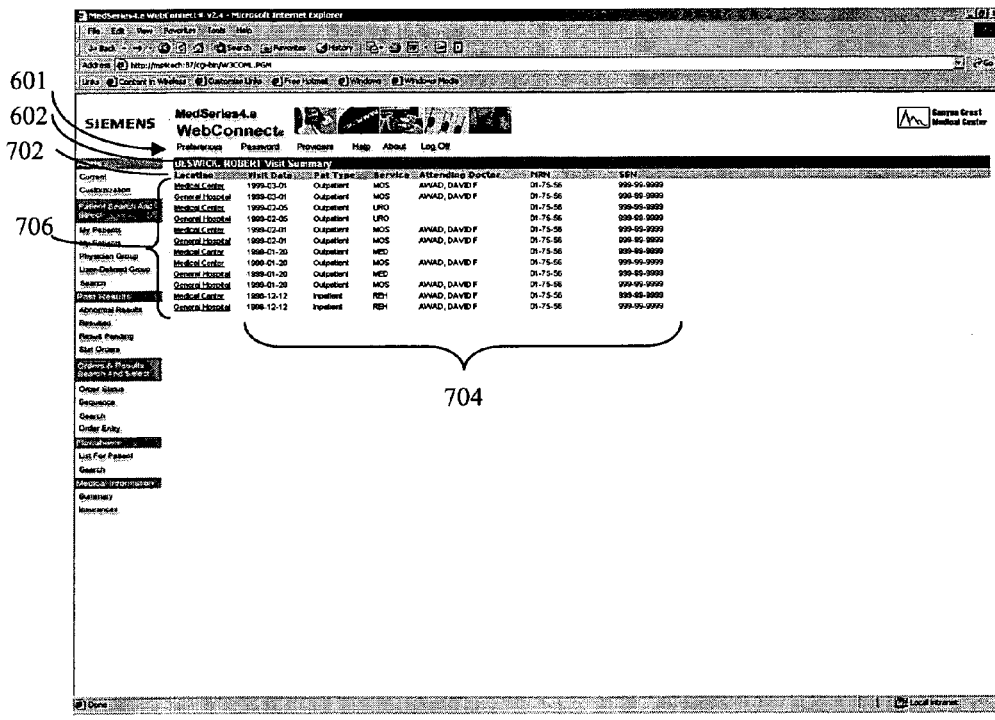
FIG. 7 illustrates a display window showing a list of healthcare sources related to a selected patient, shown in FIG. 6, generated using the methods shown in FIG. 2 or 3, 4 and 5, in accordance with a preferred embodiment of the present invention.
Figure 8:
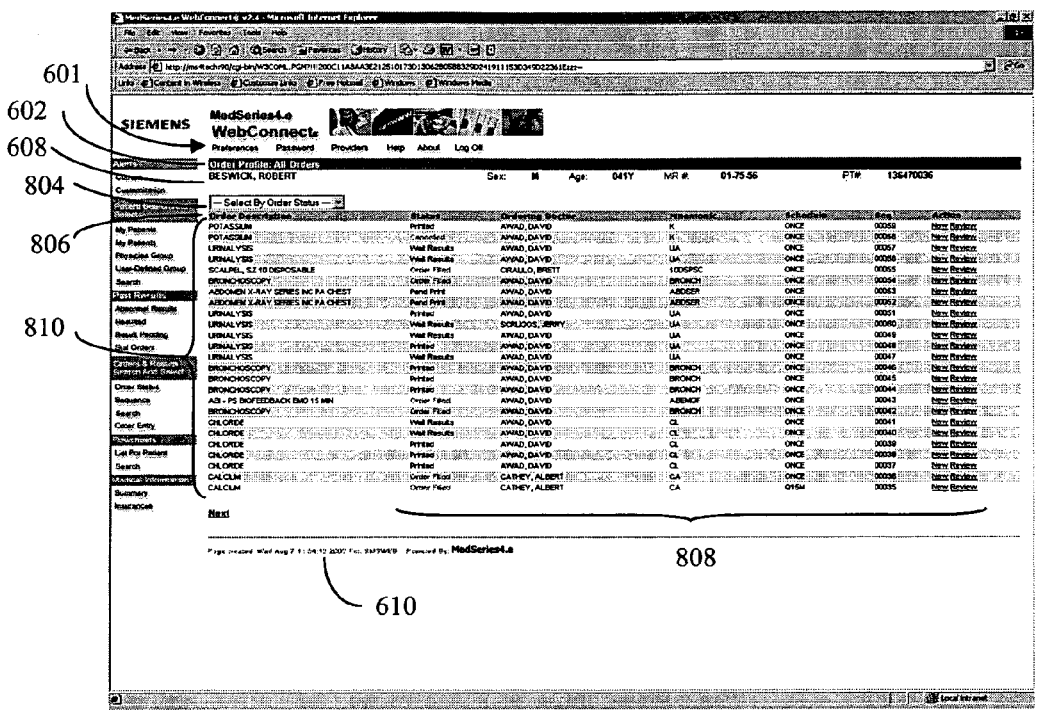
FIG. 8 illustrates a display window showing healthcare information related to a patient, shown in FIG. 6, in accordance with a preferred embodiment of the present invention.

The user interface 32 of the client device 22 generally includes an input device that permits a user to input information into the client device 22 and an output device that permits a user to receive information from the client device 22. Preferably, the input device is a keyboard, but also may be a touch screen, a microphone with a voice recognition program, for example. Preferably, the output device is a display, but also may be a speaker, for example. The output device provides information to the user responsive to the input device receiving information from the user or responsive to other activity by the client device 22. For example, the display presents information responsive to the user entering information in the client device 22 via the keypad. Preferably, a web browser forms a part of each of the input device and the output device by permitting information to be entered into the web browser and by permitting information to be displayed by the web browser, as shown in FIGS. 6, 7 and 8. Each of the healthcare computer 24 and the server device 14 may also have user interfaces 38 and 48, respectively, having an input device and an output device, which operates in the same or different way than the user interface 32 of the client device 22.

The server device 14 generally includes a memory unit 46, an optional user interface 48, and a processor 50. The memory unit 46 generally includes patient information 52 and a list of available healthcare sources 54. The memory unit 46 also includes programs for running the server device 14. The server device 18 is preferably implemented as a personal computer or a workstation. Hence, the server device 18 and the computer 12 may be implemented as the same computer or separate computers. Preferably, the part of the memory unit 46 that stores the patient information 52 and the list of available healthcare sources 54 are implemented in random access memory (RAM), or other suitable memory unit that can be refreshed, cached, or updated while the server device 14 is in use. Preferably, the part of the memory unit 46 that holds the programs is implemented in read only memory (ROM), or other suitable memory unit that runs a predetermined program while the server device 14 is in use.

Patient information 52 in the memory 46 generally include any information related to a patient including, without limitation, biographical, financial, clinical, workflow, and care plan information. The patient information 52 may be represented in a variety of file formats including, without limitation, text files such as documents, graphic files such as a graphical trace including, for example, an electrocardiogram (EKG) trace, an electrocardiogram (ECG) trace, and an electroencephalogram (EEG) trace, video files such as a still video image or a video image sequence, an audio file such as an audio sound or an audio segment, and visual files, such as a diagnostic image including, for example, a magnetic resonance image (MRI), an x-ray, a positive emission tomography (PET) scan, or a sonogram. The patient information 52 is an organized collection of clinical information concerning one patient's relationship to a healthcare enterprise (e.g. region, hospital, clinic, or department). The patient record can narrowly be considered as a file cabinet or repository with divisions and indexing mechanisms. These divisions resemble a hierarchy with folders, documents and document components, or other objects representing collections of clinical elementary information. Such folder divisions include traditional classifications such as summaries, notes, investigations, orders, medications, correspondence, results, etc.

Preferably, the patient information 52 includes the master patient index (MPI). Examples of the patient information 52 are provided with reference to FIGS. 6, 7, and 8. The patient information 52 represents or includes the information received from each of the healthcare sources 16 that was requested by the server device 14 responsive to the initial request from the computer 12. Preferably, the memory unit 46 temporarily stores the patient information 52. Such temporary storage may also be considered virtual storage or non-permanent storage. The term "temporary" generally means to last for a limited time. The term "virtual" generally means to be in effect or essence though not formally recognized or admitted. The term "virtual storage" generally means that the memory 52 in the server device 14 is an extension of the memory in each of the healthcare sources 16. Hence, the patient information 52 may otherwise be called a virtual master patient index (VMPI) because the patient information is in effect an extension of the memory in each of the healthcare sources 16 though not formally recognized as the memory in each of the healthcare sources 16 itself.

The limited time that the memory 52 stores the patient information 52 varies depending on the particular application or implementation of the healthcare information system 10. Typically, the memory 52 stores the patient information 52 for a relatively short amount of time in the range of seconds, minutes or hours, as opposed to weeks, months or years, to permit a person who requested the patient information 52 to satisfy their request for the desired information. Preferably, the longer the patient information 52 is temporarily stored, the faster the patient information 52 is becoming outdated because the patient information 52 is not automatically refreshed without initiating a new query. However, automatic refresh of the same query may be implemented, if so desired.

The memory 46 of the server device 14 stores a limited amount of patient information 52 related to each query, as shown in FIG. 7. Preferably, memory 46 of the server device 14 stores the patient information 52 in the form of hypertext links to more detailed information stored in the memory of the healthcare sources 16. The hypertext links preferably represent links to information databases residing at various healthcare sources 16, such as medical centers or hospitals, as shown in FIG. 7. Preferably, summary patient information 52 is also stored in the memory 46 of the server device 14 to facilitate easier identification and/or comprehension of the patient information 52, without having to link to the memory of the healthcare sources 16 for confirmation. Alternatively, detailed patient information for a particular patient may also be provided, if desired and/or appropriate.

Because the memory 46 of the server device 14 stores only a limited amount of patient information 52 for a limited amount of time, the disadvantages related to present healthcare information systems are resolved. Rather than consolidating the patient information 52 from each healthcare source into one large memory unit in a server device, the present healthcare information system 10 leverages the memory from each healthcare source 16 by the server device 14 requesting and temporarily storing only the patient information 52 related to the query. Preferably, memory unit 46 stores a list of hypertext links to various healthcare sources 16 along with summary patient information related to a particular patient, as shown in FIG. 7. Hence, the memory device 46 is much smaller, less complex, less expensive, easier to maintain, always up to date, and easy to use. Typically, patient information 52 that is not related to the query is not relevant. However, if a user determines that he did not receive the desired information, then the user may enter a new query or a modified query to try to retrieve the desired information. Many different user interface techniques for searching may be implemented for efficiency and ease of use including, without limitation, subsidiary or secondary search queries, system feedback related to the query, and system prompts for building a query. Further, the user interface for entering a query, preferably a browser, may have various forms for inputting a query including, without limitation, hypertext links, Boolean logic, template fields, natural language, and stored predetermined queries. Preferably, a query is formed using a hypertext link and/or summary patient information, as shown in FIG. 6.

The list of available healthcare sources 54, otherwise called a predetermined directory of data, keeps track of all of the healthcare sources 16 that are available to interface with the server device 14. The list 54 may be updated using a manual or an automatic registration procedure. Responsive to the list 54, the server device 14 knows which available healthcare sources to query and knows which available healthcare sources 16 to expect a response from, as described in FIG. 4. The list 54 is optional depending on how the network 20 is implemented. For example, if the network 20 were a closed network, such as a local area network (e.g., an intranet), then the server device 14 would send a query to each healthcare source 16 on the network 20, without reference to a list. Alternatively, if the network 20 is an open network, such as a wide area network (e.g., an internet), then the server device 14 would send a query to each healthcare source 16 on the network 20 responsive to the list 54.

The processor 50, otherwise called a virtual master patient index (VMPI) agent, manages the communications between the computer 12 and the healthcare sources 16 for the server device 14. The processor 50 may be implemented in software and/or hardware and operates responsive to the programs stored in the memory unit 46.

The healthcare sources 16 are sources, otherwise known as individual systems themselves, that need access to information or provide information related to the health and/or welfare of people in the care of the healthcare provider. Examples of the healthcare sources 16 include, without limitation, a hospital system 26, a medical system 28, and a physician system 30, as shown in FIG. 1, but may also include a records system, a radiology system, an accounting system, a billing system, and any other system required or desired in a healthcare information system. The hospital system 26 includes, without limitation, a lab system 56, a pharmacy system 58, a financial system 60, and a nursing system 62. The medical system 28, otherwise called an enterprise, represents a healthcare clinic or another hospital system. The physician system 30 represents a physician's office. Typically, the systems in the hospital system 26 are physically located within the same facility or on the same geographic campus. However, the medical system 28 and the physician system 30 are each typically located in a different facility at a different geographic location. Hence, the healthcare sources 16 represent multiple, different healthcare sources that may have various physical and geographic locations.

The first network 18 provides a communication network among one or more client devices 22 or healthcare computers 24 and server device 14. The second network 20 provides a communication network between the server device 14 and the healthcare sources 16. The first network 18 and the second network 20 may be the same or different network, depending on the particular network configuration and the particular communication protocols implemented. One or both of the first network 18 and the second network 20 may be implemented as a local area network (LAN), such as an intranet, or a wide area network (WAN), such as an Internet, or a combination thereof. Preferably, the first network 18 and the second network 20 are each WANs formed by the Internet.

Each of the computer 12 and the server device 14 communicates a query, otherwise called a message, and each of the server device 14 and the healthcare sources communicates a reply, otherwise called a response message, over a communication path coupled to the appropriate network 18 or 20. The client device 22 sends a query 64 and receives a reply 66 over a communication path to the first network 18. The healthcare computer 24 sends a query 68 and receives a reply 70 over a communication path coupled to the first network 18. The server device 14 receives a query 72 and sends a reply 74 over a communication path coupled to the first network 18. The server device 14 sends a query 76 and receives a reply 78 over a communication path coupled to the second network 20. The lab system 56 receives a query 80 and sends a reply 82 over a communication path coupled to the second network 20. The pharmacy system 58 receives a query 84 and sends a reply 86 over a communication path coupled to the second network 20. The financial system 60 receives a query 88 and sends a reply 90 over a communication path coupled to the second network 20. The nursing system 62 receives a query 92 and sends a reply 94 over a communication path coupled to the second network 20. The medical system 28 receives a query 96 and sends a reply 98 over a communication path coupled to the second network 20. The physician system 30 receives a query 100 and sends a reply 102 over a communication path coupled to the second network 20. Preferably, all of the replies from the healthcare sources 16 to the server device 14 are in XML format.

Each of the communication paths are preferably adapted to use one or more data formats, otherwise called protocols, depending on the type and/or configuration of the various elements in the healthcare information systems 10. Examples of the information system data formats include, without limitation, an RS232 protocol, an Ethernet protocol, a Medical Interface Bus (MIB) compatible protocol, an Internet Protocol (I.P.) data format, a local area network (LAN) protocol, a wide area network (WAN) protocol, an IEEE bus compatible protocol, and a Health Level Seven (HL7) protocol. Preferably, the communication paths use an I.P. data format to permit the computer 12, the server device 14, and the healthcare sources 16 to communicate with each other using a common data format.

The I.P. data format, otherwise called an I.P. protocol, uses IP addresses. Examples of the I.P. addresses include, without limitation, Transmission Control Protocol Internet Protocol (TCPIP) address, an I.P. address, a Universal Resource Locator (URL), and an electronic mail (Email) address. The communication paths each may be formed as a wired or wireless (W/WL) connection. Preferably, the communication paths are formed as a wired connection. In the case of a wired connection, the I.P. address is preferably assigned to a physical location of the termination point of the wire, otherwise called a jack. The jack is mounted in a fixed location near the location of the various elements. In the case of a wireless connection, I.P. addresses are preferably assigned to the various elements, since the various elements would be mobile. The wireless connection permits the person using the healthcare information system 10 to be mobile beyond the distance permitted with the wired connection.

Generally, under typical operating conditions, the computer 12 generates a query that is sent to the server device 14 via the first network 18. The server device 14 sends a query to the each of the healthcare sources 16 via the second network 20 responsive to receiving the query from the computer 12. Each of the healthcare sources 16 sends a reply to the server device 16 via the second network 20 responsive to receiving the query from the server device 14. The server device 14 sends a reply to the computer 12 via the first network 18 responsive to receiving the reply from each of the healthcare sources 16. Hence, the server device 14, via the first network 18 and the second network 20, manages communications and conveys information between the computer 12 and each of the healthcare sources 16. Further details related to the method of operation of the client device 22, the healthcare computer 24, the server device 14, and the healthcare source 16, are described with reference to FIGS. 2, 3, 4, and 5, respectively.

More particularly, the server device 14 implements the VMPI agent on a Microsoft Internet Information Services (IIS) web server using Active Server Page code. The VMPI agent could also be implemented on an Apache, Tomcat, or IBM WebSphere® web server using Java code. Preferably, the VMPI agent presents a simple HTML form to the user to request the patient information, as described with reference to FIG. 6. When the user submits the form, the VMPI agent reads the healthcare source list 54 and passes the patient information to each healthcare source 16. Preferably, this is done via hypertext transfer protocol (HTTP) by appending the information as part of the uniform resource locator (URL). The VMPI agent takes the returned XML data, merges it, sorts it by date, for example, then uses XSL to transform the XML into HTML for display to the user on the client device 22. Communications with the VMPI agent could also be implemented as a web service using simple object access protocol (SOAP), and requests from the computer 12 could be implemented with the query in XML. The use of XML allows easy data transfer between dissimilar computer systems and also makes possible communications with protocols other than HTTP, including simple mail transfer protocol (SMTP), if appropriate.

Figure 2:
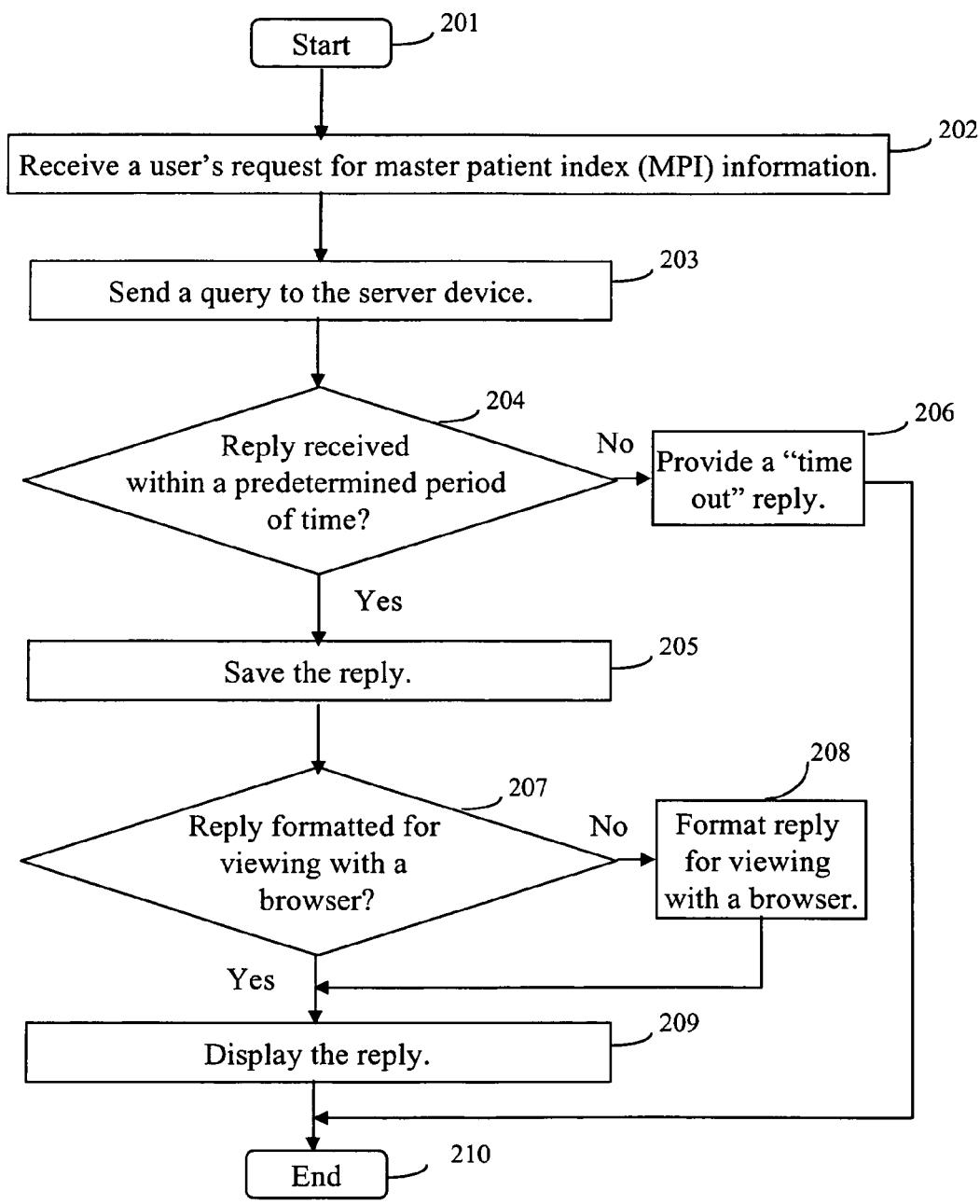
FIG. 2 illustrates a method for operating the computer, shown in FIG. 1, implemented as a client device, in accordance with a preferred embodiment of the present invention.

FIG. 2 illustrates a method 200 for operating the computer 12, shown in FIG. 1, implemented as the client device 22, in accordance with a preferred embodiment of the present invention. Preferably, the processor 34 implements the method 200 responsive to a computer program stored in the memory unit 36.

At step 201, the method begins, typically by powering on the client device 22 and by starting the MPI search software.

At step 202, the client device 22 receives a user's request for MPI information. Preferably, the user's request is received via the user interface 32 having the keyboard and the display integrated with browser software, such as Netscape® or Internet Explorer®. The request includes, for example, a patient name, a birth date, etc., as shown in FIG. 6. Preferably, the user request MPI information by clicking on a patient's name, representing a hypertext link, as shown in FIG. 6.

At step 203, the client device 22 sends a query 64 to the server device 14 responsive to receiving the user's request. The client device 22 sends the query 64 responsive to the user selecting a hypertext link, an enter function, a search function, or a find function on the keyboard or in the browser interface, for example, after the query has been entered or selected. Preferably, the query 64 is sent responsive to the user selecting a clicking on a patient's name, representing a hypertext link, as shown in FIG. 6, in combination with the client device 22 also using some or all of the summary patient information, associated with the selected patient, as shown in FIG. 6. Preferably, the query 64 is automatically built and sent by appending the hypertext and summary patient information to the uniform resource locator (URL). The query 64 is sent responsive to the user selecting a patient by clicking on a patient's name, representing a hypertext link, as shown in FIG. 6, in combination with the client device 22 also using some or all of the summary patient information, associated with the selected patient, as shown in FIG. 6. The query 64 is automatically built and sent by appending the hypertext and summary patient information to the uniform resource locator (URL) address identifying the VMPI process on the server device 14.

At step 204, the client device 22 determines whether the client device 22 receives a reply from the server device 14 within a predetermined period of time. If the client device 22 determines that it received the reply within the predetermined period of time, then the method continues to step 205; otherwise, the method continues to step 206. The predetermined period of time may be any value and may be fixed or variable, depending on various design implementations of one or more elements of the hospital information system 10, shown in FIG. 1. Preferably, the predetermined period of time is chosen to be a reasonable amount of time for the elements of the hospital information system 10 to perform, without unduly delaying feedback for the user.

At step 205, the client device 22 saves the reply 66 received from the server device 14. Preferably, the reply is temporarily saved in RAM in the memory 36.

At step 206, the client device 22 provides a "time out" reply. The time out reply provides feedback to the user that a reply to the user's query was not received in the predetermined period of time. This feedback may indicate that the first and/or second network is running at a slow speed, or that the server device 14 is not operating properly. The user may choose to reenter the query immediately or at another time, or to investigate a potential problem with the healthcare information system 10.

At step 207, the client device 22 determines whether the reply is formatted for viewing with a browser. If the client device 22 determines that the reply is formatted for viewing with a browser, then the method continues to step 209; otherwise, the method continues to step 208. The determination at step 207 depends on whether or not the server device 14 performed this formatting before sending the reply.

At step 208, the client device 22 formats the reply for viewing with a browser. Preferably, this formatting involves converting XML to HTML.

At step 209, the client device 22 displays the reply on the display. Preferably, the reply is displayed in the browser window displayed on the display, as shown in FIGS. 7, and 8. After displaying the reply, as shown in FIG. 7, a user of the client device 22 may then select one of the healthcare source locations, representing a hypertext link, related to a particular patient to directly access detailed patient information stored at the healthcare source 16. By selecting the hypertext link for the healthcare source 16, provided by the server device 14, to communicate over the Internet, the client device 22 advantageously bypasses the server device 14 to access the detailed patient information at the healthcare source 16.

At step 210, the method ends, typically by clearing the query, ending the MPI search program, or by turning off the client device 22.

Figure 3:
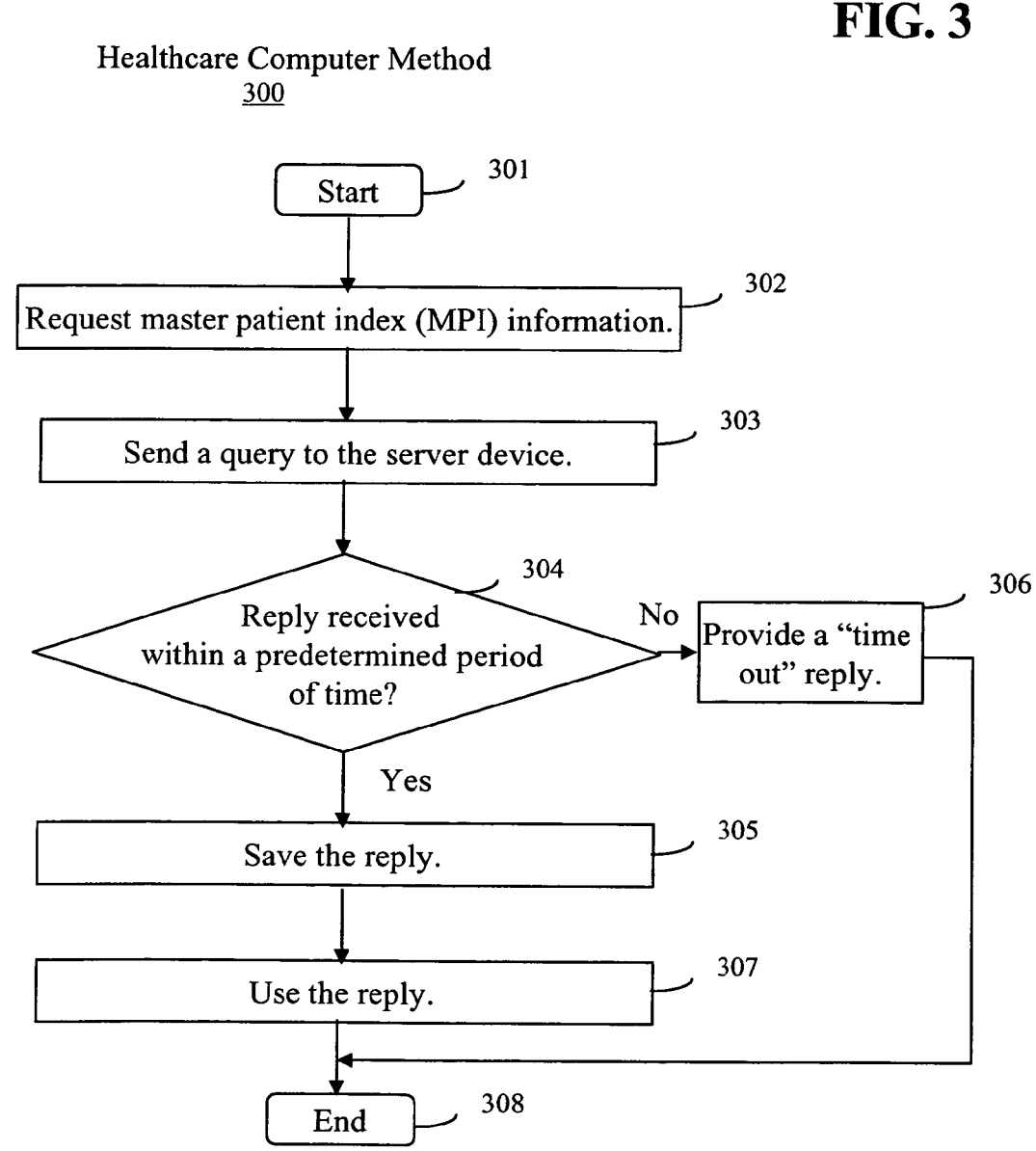
FIG. 3 illustrates a method for operating the computer, shown in FIG. 1, implemented as a healthcare computer, in accordance with a preferred embodiment of the present invention.

FIG. 3 illustrates a method 300 for operating the computer 12, shown in FIG. 1, implemented as the healthcare computer 24, in accordance with a preferred embodiment of the present invention. Preferably, the processor 40 implements the method 300 responsive to a computer program stored in the memory unit 42.

At step 301, the method begins, typically by powering on the healthcare computer 24 and by starting the MPI search software.

At step 302, the healthcare computer 24 requests MPI information from the server device 14. The request includes, for example, a patient name, a birth date, etc., and may include a hypertext link, as in step 202 described above. Preferably, the request is automatically generated by the healthcare computer 24 responsive to a predetermined computer program stored in the memory unit 42. In this case, the healthcare computer 24 may automatically request the MPI information for the purpose of generating various types of reports.

At step 303, the healthcare computer 24 sends a query 68 to the server device 14 responsive to receiving the request at step 302. Preferably, the healthcare computer 24 sends the query 68 responsive to the processor 40 automatically approving the completion of the request. Preferably, the query 68 is automatically built and sent by appending a hypertext and summary patient information to a uniform resource locator (URL).

At step 304, the healthcare computer 24 determines whether the healthcare computer 24 received a reply from the server device within a predetermined period of time responsive to sending the query at step 303. If the healthcare computer 24 determines that it received the reply within the predetermined period of time, then the method continues to step 305; otherwise, the method continues to step 306. The predetermined period of time may be any value and may be fixed or variable, depending on various design implementations of one or more elements of the hospital information system 10, shown in FIG. 1. Preferably, the predetermined period of time is chosen to be a reasonable amount of time for the elements of the hospital information system 10 to perform, without unduly delaying feedback for the healthcare computer 24.

At step 305, the healthcare computer 24 saves the reply responsive to determining that the reply was received within the predetermined period of time at step 304. Preferably, the reply is temporarily saved in RAM in the memory 42.

At step 306, the healthcare computer 24 provides a "time out" reply responsive to determining that the reply was not received within the predetermined period of time at step 304. The time out reply provides feedback to the healthcare computer 24 that a reply to the healthcare computer's query was not received in the predetermined period of time. This feedback may indicate that the first and/or second network is running at a slow speed, or that the server device 14 is not operating properly. The healthcare computer 24 may be programmed to reenter the query immediately or at another time, or to alert a person to investigate a potential problem with the healthcare information system 10.

At step 307, the healthcare computer 24 uses the reply responsive to saving the reply at step 305. After saving the reply a user of the healthcare computer 24 may then automatically select one of the healthcare source locations, representing a hypertext link, for example, related to a particular patient to directly access detailed patient information stored at the healthcare source 16. By selecting the hypertext link for the healthcare source 16, provided by the server device 14, to communicate over the Internet, the healthcare computer 24 advantageously bypasses the server device 14 to access the detailed patient information at the healthcare source 16.

At step 308, the method ends, typically by clearing the query, ending the MPI search program, or by turning off the healthcare computer 24.

Figure 4:
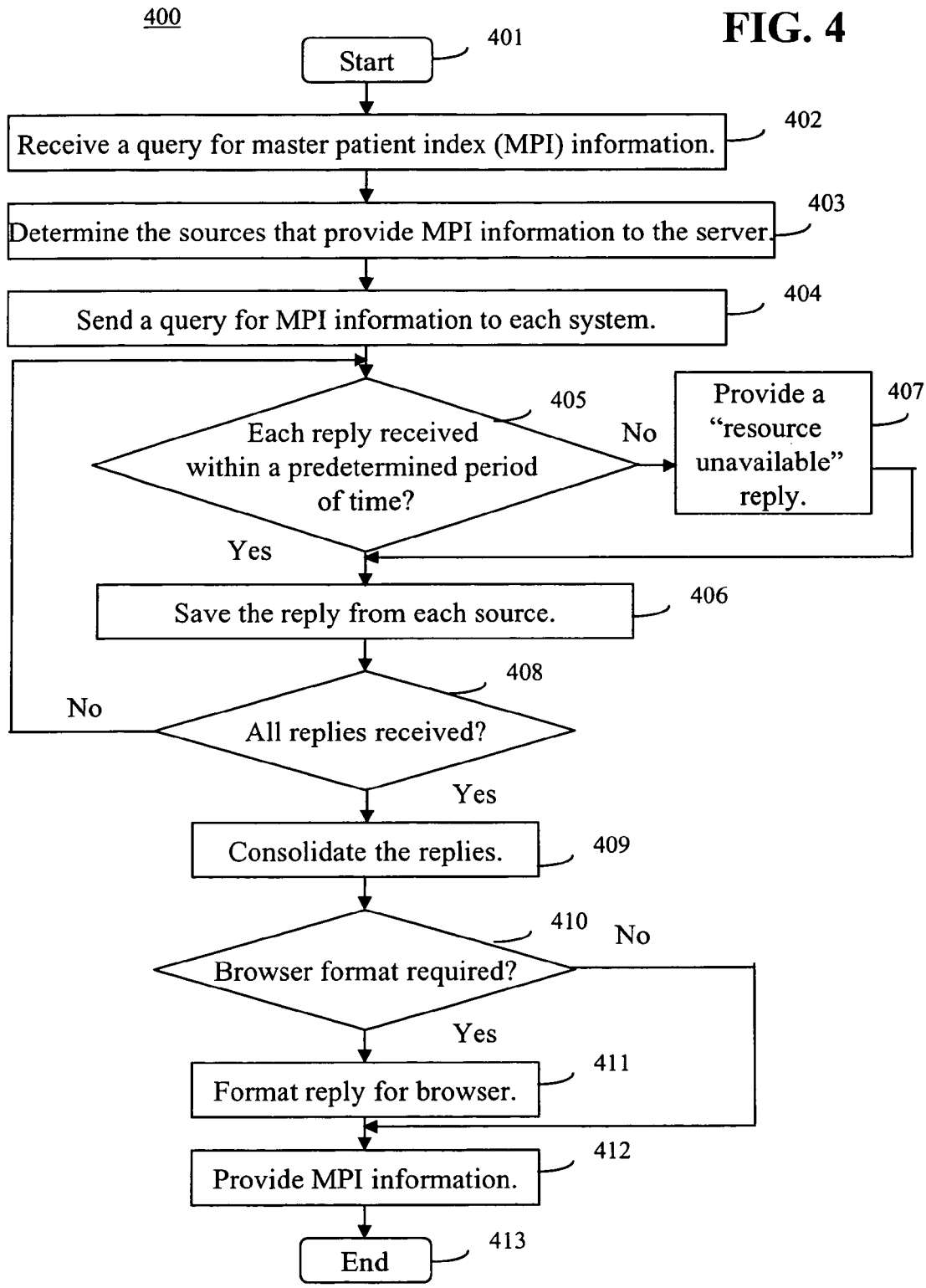
FIG. 4 illustrates a method for operating the server device, shown in FIG. 1, in accordance with a preferred embodiment of the present invention.

FIG. 4 illustrates a method 400 for operating the server device 14, shown in FIG. 1, in accordance with a preferred embodiment of the present invention. Preferably, the processor 50 implements the method 400 responsive to a computer program stored in the memory unit 46.

At step 401, the method begins, typically by powering on the server device 14 and by starting the MPI search software.

At step 402, the server device 14 receives a query 72 for the MPI information from the computer 12, implemented as the client device 22 or the healthcare computer 24, as described above with reference to FIGS. 2 and 3, respectively. The query 72 includes, for example, a patient name, a birth date, etc., included in the query sent from the computer 12.

At step 403, the server device 14 determines the healthcare sources 16 available to provide MPI information to the server device 14 responsive to receiving the query at step 402. As mentioned above, this step 403 is optional depending on the implementation of the hospital information system 10. If this step 403 is implemented, various communications between the computer 12 and the server device 14 may occur, depending on the content of the list of the available healthcare systems 54 and the content of the query 72. For example, if the query specifically request information from a healthcare source that is not part of the healthcare information system 10, then the server device 14 may provide feedback to the computer 12 indicating the same.

At step 404, the server device 14 sends a query 76 for MPI information to each of the healthcare sources 16 responsive to determining the available healthcare sources 16 at step 403. Preferably, the server device 14 sends the query 76 responsive to the processor 50 acting on commands from the computer program stored in the memory unit 46. Preferably, the query 76 is automatically built and sent by appending the patient information to a uniform resource locator (URL).

At step 405, the server device 14 determines whether the server device 14 received a reply from each of the healthcare sources 16 within a predetermined period of time responsive to sending the query to each of the healthcare sources 16 at step 404. If the server device 14 determines that it received a reply from each of the healthcare sources 16 within the predetermined period of time, then the method continues to step 406; otherwise, the method continues to step 407. The predetermined period of time may be any value and may be fixed or variable, depending on various design implementations of one or more elements of the hospital information system 10, shown in FIG. 1. Preferably, the predetermined period of time is chosen to be a reasonable amount of time for the elements of the hospital information system 10 to perform, without unduly delaying feedback for the server device 14.

At step 406, the server device 14 saves the reply received from each healthcare source 16 responsive to the server device 14 determining that it received a reply from each of the healthcare sources 16 within the predetermined period of time at step 405. The reply from a healthcare source 16 may represent patient information or a "resource unavailable" response. Hence, the server device 14 advantageously provides the computer 12 with positive feedback including patient information from healthcare sources 16 that replied and from those that didn't or couldn't to give the user the highest level of confidence possible in the patient information provided. Preferably, the reply is temporarily saved in RAM in the memory 42.

At step 407, the server device 14 provides a "resource unavailable" reply responsive to the server device 14 determining that it did not receive a reply from some of the healthcare sources 16 within the predetermined period of time at step 405. The resource unavailable reply provides feedback to the server device 14 that a reply to the server device's query was not received in the predetermined period of time. This feedback may indicate that the second network is running at a slow speed, or that one or more of the healthcare sources 16 are not operating properly. The server device 14 may be programmed to reenter the query immediately or at another time, or to alert a person to investigate a potential problem with the healthcare information system 10. After step 407, the method 400 proceeds to step 406.

At step 408, the server device 14 determines whether replies from each of the healthcare sources 16 have been received within the predetermined period of time responsive to the server device 14 saving the reply received from each healthcare source 16 at step 406. If the server device 14 determines that it received a reply from each of the healthcare sources 16, then the method continues to step 409; otherwise, the method returns to step 405 to wait for the replies from the healthcare sources 16 that have not been received within the predetermined period of time.

At step 409, the server device 14 consolidates the replies received from each of the healthcare sources 16 responsive to the server device 14 determining that a reply has been received from each of the healthcare sources 16 at step 408. The term "consolidate" generally means to combine the various replies, and may include, without limitation, sorting, manipulating, formatting, purging duplicate data, merging, and organizing the information. Hence, the server device 14 combines the received information in a way that is easy for the computer to understand and work with, or in a user selected format.

At step 410, the server device 14 determines whether the consolidated replies should be formatted for a browser. If the server device 14 determines that the browser format is required, then the method continues to step 411; otherwise, the method continues to step 412. This determination may depend on the type of computer 12 that sent the initial query.

At step 411, the server device 14 formats the consolidated replies for the browser responsive to the server device 14 determining that the browser format is required at step 410. Preferably, this formatting involves converting XML to HTML.

At step 412, the server device 14 provides the MPI information, with the browser format, responsive to the server device 14 determining that the browser format (i.e., HTML) is required at step 410. Alternatively, at step 412, the server device 14 provides the MPI information, without the browser format (i.e., XML), responsive to the server device 14 determining that the browser format is not required at step 410.

At step 413, the method ends, typically by ending the MPI search program, or by turning off the healthcare source 16.

Figure 5:
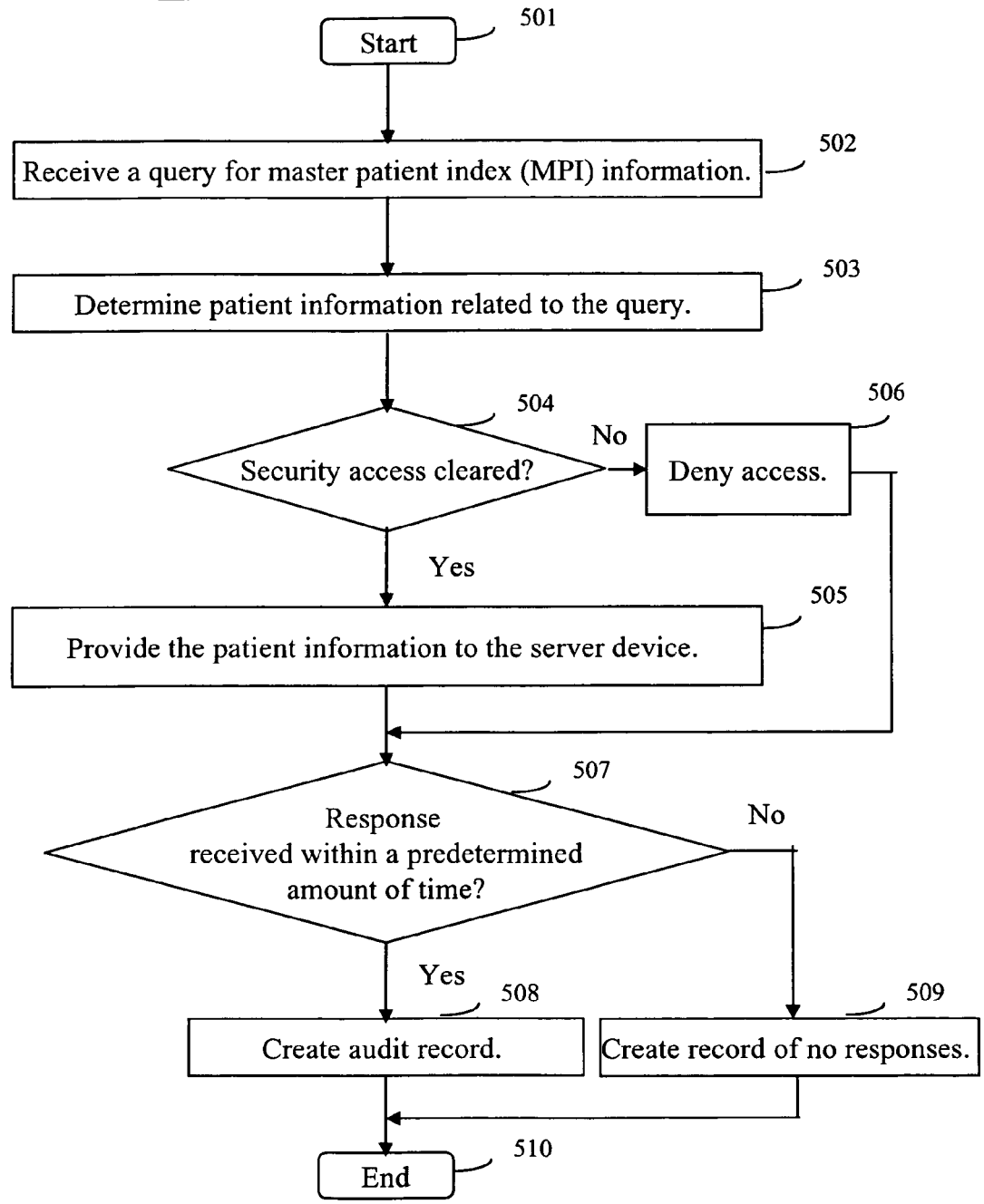
FIG. 5 illustrates a method for operating each of the healthcare sources, shown in FIG. 1, in accordance with a preferred embodiment of the present invention.

FIG. 5 illustrates a method 500 for operating each of the healthcare sources 16, shown in FIG. 1, in accordance with a preferred embodiment of the present invention. Preferably, a processor in each of the healthcare sources 16 implements the method 500 responsive to a computer program stored in a memory unit in each of the healthcare sources 16.

At step 501, the method begins, typically by powering on the healthcare sources 16 and by starting the MPI search software.

At step 502, the healthcare source 16 receives a query 80, 82, 88, 92, 96, or 100 for MPI information from the server device 14, via query 76.

At step 503, the healthcare source 16 determines the patient files that are related to the query responsive to receiving the query at step 502. This step may be implemented using various types of matching and search functions that are well known to those in the relevant art.

At step 504, the healthcare source 16 determines whether the requesting device (i.e., the computer 12 and/or the server device 14 or the user thereof) of the query has proper security level to access the patient information responsive to the determination at step 503. If the healthcare source 16 determines that the requesting device of the query has proper security level to access the patient information (i.e., cleared access), then the method continues to step 505; otherwise, the method continues to step 506. Step 504 ensures that the requesting devices that are requesting confidential patient information have a legal right to receive it. The security may be implemented using various methods well known to those skilled in the relevant art including, without limitation, passwords, computer addresses, digital certificates, and secure communication links, such as a Secure Socket Layer (SSL). Step 504 is optional depending on the particular implementation for various levels of security in the hospital information system 10. For example, if the second network 20 is a closed network, then network security may not be needed. However, in the closed network case, user security may still be required. By contrast, in a second example, if the second network 20 is an open network, such as the Internet, then network security is preferably required. However, in the open network case, user security may not be required if the computer 12 is in a secure area, such as a records office, where all users in the secure area have permission to access the patient files.

At step 505, the healthcare source 16 provides the requested patient information to the server device 14 responsive to determining that the source of the query has the proper security level to access the patient information at step 504. Preferably, the patient information includes a summary of patient information and links to corresponding patient files.

At step 506, the healthcare source 16 denies access to the patient information responsive to determining that the source of the query does not have the proper security level to access the patient information (i.e., access not cleared) at step 504.

At step 507, the healthcare source 16 determines whether the healthcare source 16 receives a response from the server device 14 within a predetermined period of time responsive to providing the patient information to the server device 14. If the healthcare source 16 receives the response from the server device 14 within the predetermined period of time, then the method continues to step 508; otherwise, the method continues to step 509. The predetermined period of time may be any value and may be fixed or variable, depending on various design implementations of one or more elements of the hospital information system 10, shown in FIG. 1. Preferably, the predetermined period of time is chosen to be a reasonable amount of time for the elements of the hospital information system 10 to perform, without unduly delaying feedback for the healthcare source 16. Step 506 is optional, if no feedback from the server device 14 to the healthcare sources 16 is required. If step 506 is not used, then step 509 is also not used because no responses would be received. However, step 508 could still be used, without step 506, to create an audit record of the patient information provided.

At step 508, the healthcare source 16 creates a record of the information provided to the server device 14 and the response received from the server device 14. The record could include information such as what files were accessed, what information was provided, what server device 14 requested and/or received the information, what security information was provided, what the query was, when the query was received, when the information was provided, etc. Preferably, the record is used to support an audit for security and information distribution purposes.

At step 509, the healthcare source 16 creates a record of the healthcare source 16 not receiving a response from the server device 14. This step 509 may indicate that the server device 14 did not receive the reply, thereby representing a problem with the server device 14 and/or the second network 20 that may need to be investigated.

At step 510, the method ends, typically by ending the MPI search program, or by turning off the healthcare source 16.

FIG. 6 illustrates a display window 600 showing a patient list, in accordance with a preferred embodiment of the present invention. The display window 600 represents patient information displayed by the browser page of the client device 22 responsive to searching patient information stored locally with the client device 22 or associated system. The display window 600 generally includes a menu 601, a title bar 602, a patient name title 604, various titles related to the patient name 606, various links to files for individual patients 608, and a date/time note 610.

The menu 601 includes, without limitation, selections such as preferences, password, providers, help, about, and log off that are related to the operation of the MPI search program. The title bar 602 represents the content of the present browser page. The patient name title 604 represents a column of the list of patient names retrieved responsive to a query. The various titles related to the patient name 606 include, without limitation, room and bed, age, the medical record number (MRN), date of birth (DOB), admission date, sex, doctor, account number, and action. Hence, the various titles related to the patient name 606 represent the summary of patient information. The various links to files for individual patients 608 are indicated by an underlined patient's name and "MPI" next to the patient's name. The "MPI" in front of the name is used as the link to start and get the patient information 52 by sending a request to the server device 14. In the case of the first and second networks being an Internet, selecting a link for an individual patient causes the computer 12 to send a query to the server device 14 to retrieve the desired information. The date/time stamp 610 indicates when the present browser page was created, thereby providing an indication of how fresh or recent the patient information is.

FIG. 7 illustrates a display window 700 showing a list of healthcare sources 16 related to a patient, shown in FIG. 6, in accordance with a preferred embodiment of the present invention. The display window 700 opens by selecting one of the links for the patient name in FIG. 6, e.g., by selecting the patient name "Beswick, Robert." The display window 700 represents the MPI information displayed by the browser page of the client device 22 responsive to sending the query 64 to the server device 14. The display window 700 includes patient information acquired by the server device 14 from the multiple, different healthcare sources 16. The display window 700 generally includes the menu 601, as described in FIG. 6, the title bar 602, as describe in FIG. 6, a location title 702, various titles related to the location 704, and various links to files for individual healthcare sources 16.

The location title 702 represents a column of the list of locations retrieved responsive to selecting the link for a patient's name. The various titles related to the location 704 include, without limitation, a visit date, a patent type, a service, an attending doctor, a medical record number (MRN), and a social security number (SSN). Hence, the various titles related to the location 704 also represent the summary of patient information. The various links to files for individual healthcare sources 16 are indicated by an underlined healthcare source. A date/time stamp may also be present on this page.

FIG. 8 illustrates a display window 800 showing healthcare information related to a patient, shown in FIG. 6, in accordance with a preferred embodiment of the present invention. The display window 800 opens by selecting a location 704, representing a healthcare source 16, from display window 700. The location includes a link to the detailed patient information stored by one of the healthcare sources 16. Preferably, the client device 12 receives detailed patient information directly from the healthcare source 16, rather than by communicating through the server device 14. The display window 800 generally includes the menu 601, as described in FIG. 6, the title bar 602, as describe in FIG. 6, the date/time note 610, as describe in FIG. 6, a drop down menu 804, an order description title 806, various titles related to the order description title 808, and various individual orders 810.

The drop down menu 804 provides various selections for sorting patient related information in the browser page. The order description title 806 represents a column of the list of orders retrieved responsive to selecting the order status from the drop down menu 804. The various titles related to the order description title 808 include, without limitation, status, ordering doctor, mnemonic, schedule, sequence, and action. The various individual orders 810 represent the orders for procedures performed on a particular patient.

FIGS. 6, 7, and 8 represent only a few of the many browser page formats and information content that may be implemented. The healthcare information system 10 may also processes other types of patient, clinical, financial, and scheduling information including, without limitation, the following:

encounter summary data about a patient visit such as visit date and time, service, patient type (emergency room, outpatient, or inpatient) and diagnosis;

results summary data about a patient such as does the patient have laboratory test, radiology tests, orders, nursing notes, progress notes, dictation, pharmacy orders, clinical alerts, allergies and any corresponding results;

scheduling information about a patient such as next appointment, last appointment and appointment history;

billing information such as insurance carriers, billing history, paid amounts, billed amounts, billing notes, and other related information;

collection based information such as collector assigned, amount sent to collections, payment history, previous collection activities, guarantor contact summary, and detailed call log information;

all data known about the patient returned as links to the data contents;

all data known about the patient returned with full data content in the response message; and a search for specific patient information such as a specific lab test result with an intelligent agent, which would be used to remove complexity from the search.

In summary of the preferred embodiments of the present invention, the healthcare information system 10 creates a virtual master patient index (VMPI) from the available healthcare sources 16, as requested by the server device 14. The VMPI information for each individual patient is created, on an as needed basis. By avoiding the creation of a single database, all of the code, management, procedures, tools, and computer systems required for patient matching and other management tasks are eliminated. Each healthcare sources 16 stores the data related to each patient and source address, such as a web address uniform resource locator (URL) is returned for each healthcare source 16 that contains additional patient information. This allows a consolidated view of a single patient's data across multiple, different healthcare sources 16, without the overhead creating and maintaining a single patient index database.

The needs for powerful processors and large memory capacity are eliminated, due to the elimination of a consolidated central database. The requirement to have complex patient matching logic in creating a consolidated central database is eliminated, since there is no common patient database repository.

The patient medical information is current and up to date, since the information is coming directly from the healthcare sources 16. There are no requirements for batch loading via batch, magnetic tape, diskette, or other communication methods and their associated costs and complexity.

The patient data can be viewed or retrieved in its original context as provided by the healthcare sources 16. All of the patient data available on each healthcare sources 16 is potentially available. For example, a doctor can determine that an abnormal result was from the complications of an automobile accident from the context of the information.

Hence, the healthcare information system 10 produces superior performance over previous systems since it requires substantially less computer hardware, software, human and technical resources. The healthcare information system 10 provides a dynamic VMPI implementation that eliminates the prior need for a separate super master patient index (SMPI) system.

Therefore, while the present invention has been described with reference to various illustrative embodiments thereof, the present invention is not intended that the invention be limited to these specific embodiments. For example, the architectures, windows, menus, and processes presented in FIGS. 1-8 are not exclusive. Other architectures, windows, menus, and processes may also be derived in accordance with the principles of the invention to accomplish the same objectives. Further, the inventive principles may be advantageously employed in any system and is not limited to use in the healthcare field. For example, a similar technique may be used to create an index of people with insurance, people with criminal records, and any other similar field with distributed database records. Those skilled in the art will recognize that variations, modifications, and combinations of the disclosed subject matter can be made without departing from the spirit and scope of the invention as set forth in the appended claims.

What is claimed is:

1. A method for use in a healthcare system for consolidating patient related information from multiple different sources, comprising the steps of:
   receiving patient identification data identifying a particular patient and an associated query for information concerning a particular patient;
   using a processor for generating a plurality of messages for communication to a corresponding plurality of information sources, said generated messages incorporating said particular patient identification data and a request for information concerning said particular patient;
   communicating said plurality of messages to said corresponding plurality of information sources without use of a patient index database providing information indicating said plurality of information sources contain information concerning said particular patient;
   receiving response messages containing requested information concerning said particular patient from said plurality of information sources;
   sorting and merging said requested information from said response messages to provide data representative of consolidated patient related information;
   using a processor for initiating generation of data representing a consolidated image view of information for said particular patient including user selectable links enabling access to information responsive to said query and residing at said plurality of information sources; and
   storing said consolidated patient related information in non-permanent storage wherein
   said step of communicating said plurality of messages to said corresponding plurality of information sources is performed without creating and maintaining a single centralized patient index database.

2. A method according to claim 1, wherein
   said communicating step comprises automatically building said plurality of messages by appending patient information to Universal Resource Locators.

3. A method according to claim 2, wherein
   said patient identification data includes at least one of, (a) patient name, (b) patient birth date and (c) a patient identification code and
   said patient identification code comprises at least one of, (i) a social security number, (ii) a patient identification code allocated by a health care provider, (iii) a healthcare insurance policy code associated with said particular patient and (iv) a patient identification code allocated by a government entity.

4. A method according to claim 1, wherein said consolidated patient related information is at least one of:
   (a) overwritten responsive to a fresh query comprising the plurality of messages communicated to said plurality of information sources, and
   (b) updated responsive to a second query comprising a second plurality of messages communicated to said plurality of information sources.

5. A method according to claim 1, further comprising the step of:
   time and date stamping the data representative of the consolidated patient related information.

6. A method according to claim 1, wherein
   said information concerning said particular patient comprises recorded information of encounters of said particular patient with healthcare providers and includes details of at least one of, (a) records of services provided by identified healthcare providers to said particular patient, (b) visits of said particular patient to identified healthcare providers, (c) outpatient services provided by an identified healthcare provider to said particular patient, (d) inpatient services provided by an identified healthcare provider to said particular patient.

7. A method according to claim 1, wherein
   said information concerning said particular patient comprises at least one of, (a) clinical results of said particular patient, (b) scheduling information concerning said particular patient, and (c) billing information concerning said particular patient.

8. A method according to claim 1, wherein
   said user selectable links employ Universal Resource Locators enabling user access to information responsive to said query.

9. A method according to claim 1, wherein
said associated query for information concerning said particular patient comprises a Universal Resource Locator incorporating patient specific information and including the step of
using a predetermined directory of data concerning said plurality of information sources in,
identifying said plurality of information sources, and
retrieving access information associated with individual sources of said plurality of information sources for use in establishing communication with said plurality of information sources.

10. A method according to claim 1, wherein
said request for information concerning said particular patient includes data for one of, (a) requesting all of the available information concerning said particular patient and (b) identifying and requesting a portion of the available information concerning said particular patient.

11. A method according to claim 1, wherein
said response messages are in Extensible Markup Language (XML) format and including the step of
processing said XML response messages to extract said requested information.

12. A method according to claim 1, wherein
said response message include data for initiating a procedure in a local processor.

13. A method according to claim 1, wherein
said plurality of messages incorporate user identification information.

14. A method according to claim 1, wherein
said sorting step comprises sorting said requested information by at least one of, (a) date of creation of record detailing said requested information, (b) date of patient encounter, (c) information source, (d) enterprise providing requested information and (e) enterprise providing service to said particular patient.

15. A method according to claim 1, including the step of
deleting redundant duplicate requested information.

16. A method according to claim 1, including the step of
displaying said consolidated patient related information to a user via a displayed image in response to user command.

17. A method according to claim 1, wherein
said consolidated patient related information comprises a composite record of encounters of said particular patient with healthcare providers ordered by date.

18. A method according to claim 1, including the step of
said merging step includes the step of re-formatting said received requested information.

19. A method according to claim 1, wherein
said method is performed automatically without manual intervention in response to user command.

20. A method for operating a healthcare user interface system supporting user access to consolidated patient related information derived from multiple different sources comprising the steps of:
receiving patient identification data identifying a particular patient and an associated query for information concerning a particular patient;
communicating said plurality of messages to said corresponding multiple different sources without use of a patient index database providing information indicating said multiple sources contain information concerning said particular patient; and
using a processor for initiating processing of data representative of consolidated information related to said particular patient for presentation in a displayed image including user selectable links enabling access to information responsive to said query and residing at said multiple sources in response to user command, said data representative of said consolidated information being derived by sorting and merging information in messages received in response to information request messages incorporating said particular patient identification data and a request for information concerning said particular patient; and storing said consolidated patient related information in non-permanent storage wherein
said step of communicating said plurality of messages to said corresponding plurality of information sources is performed without creating and maintaining a single centralized patient index database.

21. A method according to claim 20, wherein
said step of initiating processing of data representative of consolidated information related to said particular patient for presentation in a displayed image occurs in response to user selection of an icon in at least one of, (a) a displayed image presenting a list of patient names including said particular patient and (b) a displayed image showing a service previously provided to said particular patient.

22. A method for use in a healthcare system for consolidating patient related information from multiple different sources, comprising the steps of:
receiving patient identification data identifying a particular patient and an associated query for information concerning a particular patient;
using a processor for generating a plurality of messages for communication to a corresponding plurality of information sources, said generated messages incorporating said particular patient identification data and a request for information concerning said particular patient;
communicating said plurality of messages to said corresponding plurality of information sources without use of a patient index database providing information indicating said plurality of information sources contain information concerning said particular patient;
receiving response messages containing requested information concerning said particular patient from said plurality of information sources;
sorting and merging said requested information from said response messages to provide data representative of consolidated patient related information; and
using a processor for initiating generation of data representing a consolidated image view of information for said particular patient including user selectable links enabling access to information responsive to said query and residing at said plurality of information sources wherein
said step of generating a plurality of messages includes the step of generating an individual message to a particular information source by incorporating in a Universal Resource Locator string,
said particular patient identification data,
data representing said request for information concerning said particular patient, and
an address of said particular information source.

23. A system for use in a healthcare system for consolidating patient related information from multiple different sources, comprising:
an interface processor for,
receiving patient identification data identifying a particular patient and an associated query for information concerning a particular patient;

generating a plurality of messages for communication to a corresponding plurality of information sources, said messages incorporating said particular patient identification data and a request for information concerning said particular patient;

communicating said plurality of messages to said corresponding plurality of information sources without use of a patient index database providing information indicating said plurality of information sources contain information concerning said particular patient;

receiving response messages containing requested information concerning said particular patient from said plurality of information sources; and a data processor for sorting and merging said requested information from said response messages to provide data representative of consolidated patient related information; and initiating generation of data representing a consolidated image view of information for said particular patient including user selectable links enabling access to information responsive to said query and residing at said plurality of information sources and storing said consolidated patient related information in non-permanent storage wherein said step of communicating said plurality of messages to said corresponding plurality of information sources is performed without creating and maintaining a single centralized patient index database.

* * * * *